(12) United States Patent
Lee et al.

(10) Patent No.: US 10,266,475 B2
(45) Date of Patent: Apr. 23, 2019

(54) METHOD FOR PRODUCING ACRYLIC ACID (71) Applicants: LG CHEM, LTD., Seoul (KR); KOREA ADVANCED INSTITUTE OF SCIENCE AND TECHNOLOGY, Daejeon (KR)

(72) Inventors: Won Jae Lee, Daejeon (KR); Dong Su Song, Daejeon (KR); Yong Jin Choe, Daejeon (KR); Hyun Joo Lee, Daejeon (KR); Min Su Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/752,181

(22) PCT Filed: Jan. 31, 2017

(86) PCT No.: PCT/KR2017/001008
§ 371 (c)(1),
(2) Date: Feb. 12, 2018

(87) PCT Pub. No.: WO2017/179805
PCT Pub. Date: Oct. 19, 2017

(65) Prior Publication Data
US 2018/0237372 A1 Aug. 23, 2018

(30) Foreign Application Priority Data
Apr. 12, 2016 (KR) .................. 10-2016-0044700

(51) Int. Cl.
*C07C 51/25* (2006.01)
*C07C 51/44* (2006.01)
*C07C 51/50* (2006.01)
*C07C 57/04* (2006.01)
*B01J 23/44* (2006.01)
*B01J 23/58* (2006.01)
*B01J 23/60* (2006.01)
*B01J 23/66* (2006.01)
*B01J 23/68* (2006.01)
*B01J 23/74* (2006.01)
*B01J 23/78* (2006.01)
*B01J 23/80* (2006.01)
*B01J 23/89* (2006.01)
*B01J 35/00* (2006.01)
*B01J 35/02* (2006.01)
*B01J 35/08* (2006.01)
*B01J 37/00* (2006.01)
*B01J 37/02* (2006.01)
*B01J 23/46* (2006.01)
(Continued)

(52) U.S. Cl.
CPC ............ *C07C 51/25* (2013.01); *B01J 23/44* (2013.01); *B01J 23/46* (2013.01); *B01J 23/52* (2013.01); *B01J 23/58* (2013.01); *B01J 23/60* (2013.01); *B01J 23/66* (2013.01); *B01J 23/682* (2013.01); *B01J 23/685* (2013.01); *B01J 23/686* (2013.01); *B01J 23/688* (2013.01); *B01J 23/74* (2013.01); *B01J 23/78* (2013.01); *B01J 23/80* (2013.01); *B01J 23/89* (2013.01); *B01J 23/892* (2013.01); *B01J 23/8906* (2013.01); *B01J 23/8913* (2013.01); *B01J 23/8946* (2013.01); *B01J 23/8953* (2013.01); *B01J 35/006* (2013.01); *B01J 35/0013* (2013.01); *B01J 35/023* (2013.01); *B01J 37/0072* (2013.01); *B01J 37/0211* (2013.01); *B01J 37/16* (2013.01); *C07C 51/44* (2013.01); *C07C 51/50* (2013.01); *C07C 57/04* (2013.01); *B01J 35/08* (2013.01); *B01J 37/009* (2013.01); *B01J 2523/00* (2013.01)

(58) Field of Classification Search
CPC ......... C07C 51/50; C07C 51/44; C07C 51/25; C07C 57/04
See application file for complete search history.

(56) References Cited

U.S. PATENT DOCUMENTS

| 3,739,020 | A | | 6/1973 | McClain et al. |
| 4,051,181 | A | * | 9/1977 | Murib .................. C07C 29/095 560/243 |
| 4,552,860 | A | | 11/1985 | Murib |

(Continued)

FOREIGN PATENT DOCUMENTS

| CN | 103007929 A | 4/2013 |
| JP | 3887511 B2 | 12/2006 |

(Continued)

OTHER PUBLICATIONS

Norskov et al, Nature Chemistry, Towards the Computational Design of Solid Catalysts, 2009, 1, pp. 37-46. (Year: 2009).*

(Continued)

*Primary Examiner* — Paul A Zucker
(74) *Attorney, Agent, or Firm* — Dentons US LLP (57) ABSTRACT

A method for preparing acrylic acid, more specifically, to a method for preparing acrylic acid under a neutral condition at high yield in a short time without using a base, unlike the prior art in which a base is essentially used. The acrylic acid is produced using a supported catalyst having a specific composition when preparing acrylic acid by oxidation of allyl alcohol. Particularly, the preparation method can recover acrylic acid rather than acrylic acid salt as a final product, and thus has an advantage that the overall process cost can be reduced by eliminating essential processes in the prior art, such as ion exchange after the acidification process required for the conversion of acrylic acid salt to acrylic acid.

10 Claims, 4 Drawing Sheets

(51) Int. Cl.
   *B01J 23/52* (2006.01)
   *B01J 37/16* (2006.01)

(56) References Cited

U.S. PATENT DOCUMENTS

| | | | |
|---|---|---|---|
| 4,792,620 A * | 12/1988 | Paulik | B01J 31/0231 |
| | | | 560/232 |
| 6,429,332 B1 | 8/2002 | Tanimoto et al. | |
| 6,777,369 B1 | 8/2004 | Kuroda et al. | |
| 2014/0148616 A1 | 5/2014 | Fraga et al. | |
| 2015/0011797 A1 | 1/2015 | Whiston et al. | |
| 2015/0361021 A1 | 12/2015 | Kim et al. | |
| 2016/0096170 A1 | 4/2016 | Kim et al. | |
| 2016/0122272 A1 | 5/2016 | Lee et al. | |

FOREIGN PATENT DOCUMENTS

| | | |
|---|---|---|
| JP | 5914615 B1 | 4/2016 |
| KR | 100247524 B1 | 12/1999 |
| KR | 100264966 B1 | 9/2000 |
| KR | 101002761 B1 | 6/2009 |
| KR | 101504673 B1 | 10/2014 |
| KR | 1020150006349 A | 1/2015 |
| KR | 1020150144128 A | 12/2015 |
| KR | 1020170027208 A | 3/2017 |

OTHER PUBLICATIONS

Mario G. Clerici, et al., "Liquid Phase Oxidation via Heterogeneous Catalysis. Organic Synthesis and Industrial Applications", Angew. Chem. Int. Ed., Jul. 21, 2014, p. 7707, vol. 53, Issue 30.

Abad, et al., "Unique gold chemoselectivity for the aerobic oxidation of allylic alcohols", Chem. Commun., pp. 3178-3180, 2006.

Chun-Jiang Jia, et al., "Very Low Temperature CO Oxidation over Colloidally Deposited Gold Nanoparticles on Mg(OH)2 and MgO", J. Am. Chem-Soc, vol. 132. pp. 1520-1522, (2010).

Lopez-Sanchez, et al.: "Au—Pd supported nanocrystals prepared by a sol immobilisation technique as catalysts for selective chemical synthesis", XP055532032, Physical Chemistry Chemical Physics, vol. 10, pp. 1921-1930 (2018).

Falletta, et al.: "Enhanced Performance of the catalytic conversion of allyl alcohol to 3-hydroxypropionic acid using bimetallic gold catalysts", XP055246322, Faraday Discussions, vol. 152, pp. 367-379 (2011).

* cited by examiner

METHOD FOR PRODUCING ACRYLIC ACID

TECHNICAL FIELD

This application is a National Stage Application of International Application No. PCT/KR2017/001008, filed Jan. 31, 2017, and claims the benefit of Korean Patent Application No. 10-2016-0044700, filed Apr. 12, 2016, the contents of which are incorporated herein by reference in their entirety for all purposes as if fully set forth below.

The present invention relates to a method for preparing acrylic acid which can be prepared under the neutral condition without using a base.

BACKGROUND ART

Since acrylic acid is an organic compound which has both carboxylic acid and double bond and its structure is very simple and can be converted into various substances, thus the inherent value of acrylic acid is quite large. Among them, acrylic acid is used as a raw material for super absorbent polymer (SAP, Super Absorbent Polymer), paints, adhesives, etc., and is used as a raw material for various chemical products.

Acrylic acid is prepared by various methods, and commercially is prepared by oxidation of propylene, hydrolysis of acrylonitrile, and carbonylation of acetylene.

However, since the process uses raw materials derived from crude oil, in order to cope with the problem of crude oil depletion, a method of using biomass-derived resources as a starting material has recently been proposed. Specifically, acrylic acid is prepared through the reaction pathway of "glycerol-allyl alcohol-acrylic acid" using glycerol as a starting material (Korean patent Publication No. 2015-0006349).

In the above patent publication, the production of acrylic acid from allyl alcohol is carried out under strongly basic conditions by adding a base such as sodium hydroxide. As a result, the final substance is prepared as an acrylate salt rather than acrylic acid, and thus an additional separation step is indispensable. Also, due to the use of strong bases, there is a problem that the process equipment or apparatus used in the preparation of acrylic acid is corroded. Therefore, a method for preparing acrylic acid in neutral conditions, not strong bases, is required.

PRIOR ART LITERATURE

Patent Literature

A method for producing acrylic acid from glycerol (Korean patent Publication No. 2015-0006349)

DISCLOSURE

Technical Problem

Therefore, by conducting studies to prepare acrylic acid from allyl alcohol under the neutral condition, the present inventors prepared a catalyst exhibiting catalyst activity under the neutral condition, and as a result of carrying out the reaction using the catalyst prepared, confirmed that acrylic acid can be prepared at a high yield under the neutral condition without using a base, especially a strong base, and thus completed the present invention.

Therefore, it is an object of the present invention to provide a method for producing acrylic acid at a high yield in a short time under the neutral condition using a catalyst without using a base.

Technical Solution

In order to achieve the above object, the present invention provides a method for producing acrylic acid by the oxidation reaction of allyl alcohol in the presence of a catalyst characterized in that the oxidation reaction is carried out under the neutral condition.

At this time, it is characterized in that the oxidation reaction of allyl alcohol is carried out at pH 6-8.

It is characterized in that the catalyst is a supported catalyst in which a metal catalyst selected from the group consisting of an Au-transition metal alloy catalyst, a transition metal catalyst, and a combination thereof is supported on a support.

It is characterized in that the transition metal is any one selected from the group consisting of Ru, Rh, Pd, Os, Ir, Pt, Zn, Co, Ni, Cr, Fe, Mo, Nb, Mn and a combination thereof, preferably Pd.

In addition, it is characterized in that the support is an oxide or hydrate of any one selected from the group consisting of Mg, Al, Ca, Zn, Zr and a combination thereof, and preferably, the support is any one selected from the group consisting of MgO, $Mg(OH)_2$, $Al_2O_3$, cHT (calcined hydrotalcite), hydroxyapatite ($Ca_5(OH)(PO_4)_3$), ZnO, $Zr(OH)_2$ and a combination thereof, and most preferably, the support is MgO.

Advantageous Effects

The method for preparing acrylic acid according to the present invention can produce acrylic acid rather than acrylic acid salt as a final product by carrying out the reaction under the neutral condition. Thus, the method of the present invention has an advantage that the overall process cost can be reduced by eliminating essential processes such as ion exchange process after the acidification process required for the conversion of acrylic acid salt to acrylic acid.

In addition, the method of the present invention has an effect of eliminating the corrosion problem of equipment due to the use of a strong base and reducing the cost.

DESCRIPTION OF DRAWINGS

FIG. 4 (a) shows a spectrum obtained from HPLC (High Performance Liquid Chromatography) for the product of the oxidation reaction of allyl alcohol using the catalyst prepared in Example 3, and FIG. 4 (b) is the HPLC spectrum after 12 hours.

BEST MODE

The preparation of acrylic acid can be done in a variety of ways, but in the present invention, the preparation of acrylic acid is carried out by using allyl alcohol as a starting material and advancing the reaction path from allyl alcohol to acrylic acid. Specifically, acrylic acid is prepared by introducing (S1) raw materials (allyl alcohol, catalyst, oxidizing gas) into the reactor, (S2) performing an oxidation reaction, and (S3) separating and purifying acrylic acid.

At this time, it is characterized in that the oxidation reaction is carried out under the neutral condition, i.e., pH 6 to 8, rather than carried out in a strong base atmosphere by adding a base such as NaOH used in the prior art, and the present invention suggests an optimal catalyst suitable for this.

A catalyst has different activities under acidic/neutral/basic conditions when applied to actual chemical reactions. As a result, the catalyst may also be classified as an acid catalyst or a basic catalyst, and the basic catalyst has little or no catalytic activity under acidic conditions. The preparation of acrylic acid according to the present invention is carried out under the neutral condition rather than the conventional strong base conditions, and thus it is necessary to present a catalyst suitable for the conditions.

(S1) Input of Raw Materials

First, allyl alcohol as a starting material, the catalyst, and the oxidizing gas are introduced into the reactor.

The method and the order of introducing the allyl alcohol, the catalyst and the oxidizing gas are not particularly limited, but various input methods such as a method of introducing all at once into the reactor, a method of continuously introducing and a method in which a portion is introduced into the reactor and the remainder is continuously introduced into the reactor can be used and it is possible to use any of these methods. In an embodiment of the present invention, the catalyst is first introduced to the reactor, and then sequentially, allyl alcohol and the oxidizing gas are continuously introduced.

The allyl alcohol used as the starting material can be used without any particular limitations as long as it is usable for the preparation of acrylic acid. As an example, the allyl alcohol can be used in a concentrated form or in the form of a solution mixed with water or the like, and allyl alcohol having a purity of 60 to 99.9% can be preferably used. Also, if necessary, allyl alcohol can be prepared and used by the method described in Korean patent Publication No. 2015-0006349.

In this case, the reactor is not particularly limited in the present invention, and may be any one reactor selected from the group consisting of known batch reactors, semi-batch reactors, continuous stirred tank reactors, plug flow reactors, stationary phase reactors and fluidized bed reactors or may be a mixed reactor in which two or more of these are connected.

Particularly, for the conventional case, a base such as NaOH is added in such a raw material input step for performing the oxidation reaction in the following (S2), but for the present invention, since the base is excluded, the use of a base is unnecessary in this raw material input. The elimination of these base additions is due to the use of a certain catalyst.

The catalyst used in the present invention has catalyst activity under the neutral condition. The activity of the catalyst directly affects the conversion of allyl alcohol. The catalyst used in the present invention is a supported catalyst in which a metal catalyst is supported on a support, and at this time, the catalytic activity is influenced by parameters such as the composition of the metals used as the catalyst, the particle size, the kind of the support, and the loading amount. Preferably, there is a trend that the smaller and the more uniform the particle size of the catalyst, and the higher the loading amount, the more the catalytic activity is.

Specifically, it is possible to use any one selected from the group consisting of an Au-transition metal alloy catalyst represented by the following formula 1 according to the present invention, a transition metal catalyst, and a combination thereof:

$$Au_x\text{-}M_y \qquad \text{[Formula 1]}$$

wherein M is transition metal, and $0.01 \leq x/y \leq 100$.

The transition metal M in formula 1 can be any metal that can be used as a catalyst, and is not particularly limited in the present invention. Preferably, the transition metal may be any one selected from the group consisting of Ru, Rh, Pd, Os, Ir, Pt, Zn, Co, Ni, Cr, Fe, Mo, Nb, Mn and a combination thereof, more preferably Ru, Rh, Pd, Os, Ir or Pt, most preferably Pd.

The mole ratio (x/y) of Au and transition metal M represented by x/y in formula 1 is 0.01 to 100, preferably 0.1 to 50.

In addition, the transition metal catalyst may be a catalyst that uses the above-mentioned transition metal alone, i.e., Ru, Rh, Pd, Os, Ir, Pt, Zn, Co, Ni, Cr, Fe, Mo, Nb, or Mn, preferably Ru, Rh, Pd, Os, Ir, or Pt, most preferably Pd.

According to a preferred experimental example of the present invention, it can be seen that the Au—Pd catalyst and the Pd catalyst are used as the metal catalyst, and all of them can be used for the preparation of acrylic acid, but in terms of activity, the Pd catalyst has the best catalytic activity and thus can produce acrylic acid in high yield in a short time.

Along with the composition of these metal catalysts, particle size is also an important parameter in relation to catalytic activity.

The smaller the size of the metal catalyst particles, the higher the catalytic activity is. At this time, the more uniform the particle size, the wider the contact area with the reactive material is, and therefore, the conversion of allyl alcohol to acrylic acid is increased, and the rate of conversion is increased, thereby shortening the overall process time.

Preferably, the particle size of the metal catalyst has an average particle diameter of 1 to 50 nm, more preferably 2 to 10 nm, and has a monodispersity with a very narrow range of dispersion. The size of the catalyst particles cannot be less than 1 nm in the actual process, and when the size of the catalyst particles is larger than 50 nm, the above-mentioned effects cannot be ensured.

In addition, the supported catalyst according to the present invention is supported on a support (support element or carrier), and the support on which the metal catalyst is supported supports and disperses the metal catalyst and thus serves to increase the surface area of the catalyst, stabilize the catalyst by preventing sintering phenomenon, and lower the price of the catalyst. The support is not active by itself, but it affects the catalytic activity due to the above functions, and shows a large difference in catalyst activity depending on how much metal catalyst is supported even when the composition of the catalyst is the same, and thus the selection of the support should also be considered very important.

Possible types of supports may be oxide or hydrate of any one selected from the group consisting of Mg, Al, Ca, Zn, Zr and a combination thereof, and preferably may be any one selected from the group consisting of MgO, Mg(OH)$_2$, Al₂O₃, cHT (calcined hydrotalcite), hydroxyapatite (Ca₅(OH)(PO₄)₃), ZnO, Zr(OH)₂ and a combination thereof, and most preferably may be MgO. These supports can effectively support the metal catalyst as compared with conventional silicon oxide, cerium oxide and the like.

In addition, the specific surface area, pore volume, and average pore size of the support are important parameters for attaining a high catalyst loading amount, and it is preferable that the support has a specific surface area of 1 m²/g or more.

When the support is used, it is possible to prepare the catalyst having a loading amount of 5 wt. % or less, preferably 0.0001 to 5 wt. %. The larger the loading amount, the more favorable it is. However, the loading amount should be considered together with the reproducibility when applied to the production line, physical stability, cost, activity and selectivity of the catalyst. If the loading amount is lower than the above range, it is difficult to obtain a sufficient level of activity of the catalyst. Also, the loading higher than the above range lowers the stability of the catalyst. Therefore, it is suitably used within the above range.

The method of preparing the catalyst according to the present invention is not particularly limited, and the catalyst can be prepared by preparing a known metal catalyst and then allowing it to be carried on a support.

The method for producing the metal catalyst includes a precipitation method, a colloid method, a polyol method and the like. In the present invention, the metal catalyst is prepared using the colloidal method, which has no complicated conditions and is easy to prepare nano-sized particles, specifically a colloidal-deposition method.

In the colloidal deposition process, the reduction reaction of the precursor to the metal takes place in a micelle colloid stabilized with a dispersant rather than in the bulk mixed solution. As a result, there is an advantage that an amount of precursors participating in the reduction reaction becomes almost uniform for each micelle, and thus the particles obtained after the final reduction are produced in nano size and the distribution of the particle size is very narrow.

Figure 1:
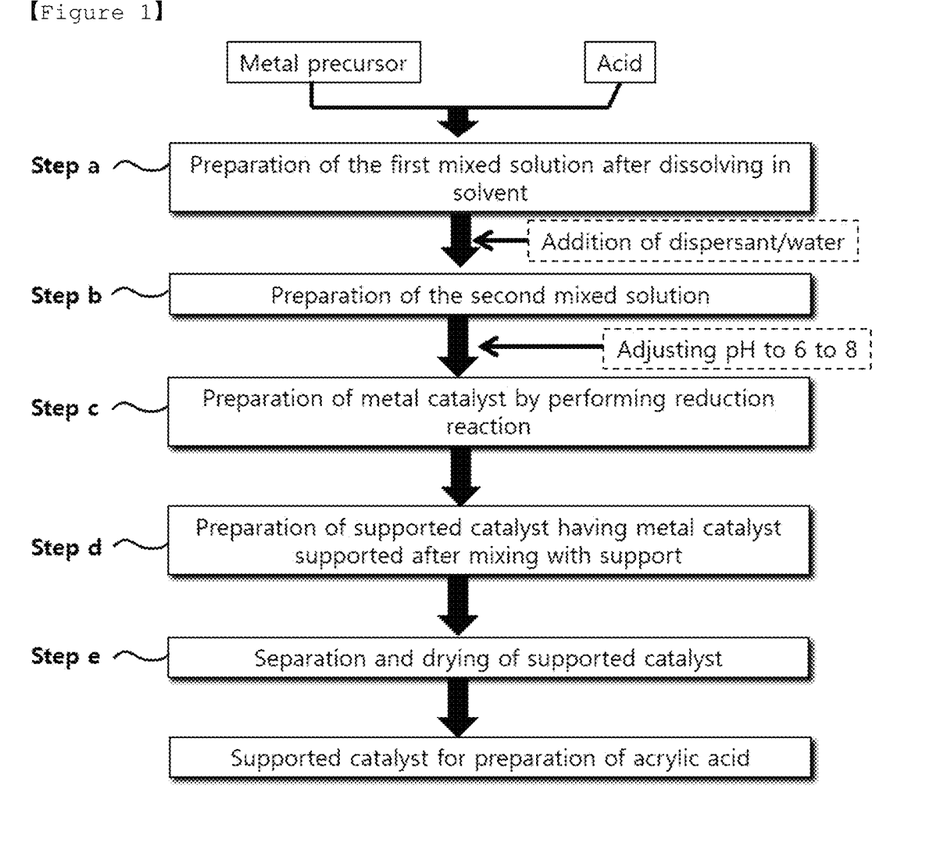
FIG. 1 is a flow chart illustrating the steps of preparing the supported catalyst according to one embodiment of the present invention.

FIG. 1 is a flow chart illustrating the steps of preparing the supported catalyst according to the present invention.

Referring to FIG. 1, the supported catalyst is prepared by the steps comprising, step (a) for preparing a first mixed solution by dissolving a metal precursor and an acid in a solvent;

step (b) for preparing a second mixed solution by adding a dispersant and water to the first mixed solution;

step (c) for preparing a metal catalyst by adjusting the pH of the second mixed solution to 6 to 8 and then performing a reduction reaction;

step (d) for adding a support to the dispersion in which the metal catalyst is dispersed, and then mixing to prepare a supported catalyst having the metal catalyst supported thereon; and step (e) for separating and drying.

Each step will be described in detail below.

First, the first mixed solution is prepared by preparing the precursor of the metal catalyst and dissolving it in the acid-added solvent (step (a)).

The metal precursor can be any precursor as long as it can be converted to the metal catalyst by the reduction reaction, and metal-containing alkoxide, acetyl acetate, nitrate, oxalate, halide, cyanide or the like can be used, preferably halide can be used.

As an example, when Au is used, the Au precursor may be HAuCl₄, HAuCl₄·3H₂O, HAuCl₄·4H₂O, AuCl₃, AuCl and the like, preferably HAuCl₄. In addition, when Pd is used, the Pd precursor may be PdCl₂, (NH₄)₂PdCl₄, Pd(NO₃)₂, Pd(NH₃)₂Cl₂, Pd(C₂H₃O₂)₂ and the like, preferably PdCl₂.

At this time, an acid is used to ionize the metal precursors and stably dissolve ionized metals in the solvent. The acid is not particularly limited in the present invention, and any known strong acid or weak acid may be used. Specifically, the acid may be hydrochloric acid, nitric acid, sulfuric acid, or acetic acid, preferably hydrochloric acid.

These precursors and acids are dissolved in the solvent to prepare the first mixed solution, and the solvent may be water, alcohols, ethers, ketones and aromatics, and specifically, water, alcohols or a mixture of water and alcohols is preferable.

The precursors present in the first mixed solution are ionized and converted into metal ions, and these metal ions are coordinated to each other to form complexes.

Next, the second mixed solution is prepared by adding the dispersing agent and water to the first mixed solution prepared in step (a) (step (b)).

The colloid deposition method used in the present invention is a method characterized by using a dispersant.

As the dispersing agent that can be used, a polymer dispersant is used, and preferably the polymer dispersant may be any one selected from the group consisting of polyallylamine hydrochloride, polyethyleneimine, polydiallyldimethylammonium chloride, polymethacryloxyethyltrialkylammonium halide, aminoethylated polyacrylamide, Hoffmann sensitivity-polyacrylamide, polyethyleneamine, starch, cationized starch, chitosan, PLL (poly L-lysine), pAMEAMA dendrimer, PLGA (poly(L-glutamic acid)), PVP (poly(1-methyl-2-vinylpyridine), poly L-ornithine, polyspermine, DEAE dextran (diethylaminoethyl dextran), and a combination thereof. More preferably starch is used.

The dispersant is used in a concentration of 0.1 to 20% by weight in the entire second mixed solution. If the content is less than the above range, it is not easy to control the size of the catalyst particles. On the contrary, even if it exceeds the above range, there is no advantage related to an effect and it is not economical. Therefore, it is suitably used within the above range.

At this time, the dispersant is used in a form dissolved in a solvent, and various solvents may be used depending on the type of the dispersant. As an example, in the embodiments of the present invention, when starch as a dispersant is used, starch is dissolved in water and then used.

Next, the metal catalyst is prepared by adjusting the pH of the second mixed solution obtained in step (b) 6 to 8, and then performing the reduction reaction (step (c)).

The pH of the second mixed solution is acidic due to the addition of acid to dissociate the metal ion and is adjusted to neutral for the reduction reaction.

The base which can be used for pH control is not particularly limited in the present invention, and bases known in the art can be used. As an example, the base may be any one selected from the group consisting of NaOH, KOH, NaHCO₃, Na₂CO₃, KHCO₃, K₂CO₃, CaCO₃ and a combination thereof.

The reduction reaction includes an alloying reaction of the metal ion in the second mixed solution, and at this time, the reaction is carried out at 30 to 200° C., preferably at 80 to 140° C. for 5 minutes to 12 hours, preferably for 30 minutes to 3 hours. The temperature and time are conditions under which the reduction reaction can sufficiently proceed, and the reaction is carried out under reflux conditions, and thus the temperature range may be changed depending on the type of the solvent. Also, if necessary, the reaction is carried out under reduced pressure to improve the reaction rate.

Through this reduction reaction, the metal catalyst is prepared, and the particle size has a nanosize of 1 to 50 nm as mentioned above.

At this time, a subsequent process of separating the metal catalyst from the dispersion and allowing it to be carried on the support is carried out or a subsequent process of allowing the colloidal state as it is to be carried on the support is carried out.

Next, the supported catalyst is prepared by adding the support to the dispersion in which the metal catalyst prepared in step c is dispersed and thus the impregnation of the support with the metal catalyst takes place (step (d)).

Before impregnating with the dispersion in which the metal catalyst is dispersed, the support is calcined under air or an inert gas at 300 to 1500° C., preferably 350 to 1000° C., more preferably 400 to 600° C. for 3 to 20 hours, preferably 5 to 15 hours to remove impurities therein.

The step of impregnating the support with the metal catalyst may be performed by wet impregnation, dry impregnation, impregnation under reduced pressure or spray drying of the mixture in slurry form or extrusion drying, but is not limited thereto. In the embodiment of the present invention, impregnation is performed by adding the support to the catalyst dispersion and then mixing them.

This impregnation can be repeated one or more times or several times to have a desired loading amount and, if necessary, heating or stirring can be additionally carried out.

Next, the acrylic acid catalyst according to the present invention is prepared through the step of separating and drying the supported catalyst obtained in step (d) (step (e)).

The drying can be carried out by a normal-pressure drying method or a reduced-pressure drying method. For example, the normal-pressure drying method is carried out at room temperature to 200° C., preferably at room temperature to 150° C., for 2 to 72 hours, preferably for 5 to 48 hours, under atmospheric pressure.

The obtained supported catalyst has a final state of a neutral state and thus can be suitably applied to the preparation of acrylic acid under the neutral atmosphere to be performed in the present invention.

It is advantageous in terms of reaction efficiency that the supported catalyst as described above is used in a molar ratio of allyl alcohol/metal catalyst of 10 to 2000 in this stage.

In addition, the oxidizing gas for the oxidation reaction in the present invention may be oxygen or an oxygen-containing gas. The partial pressure of the oxidizing gas may be arbitrarily set out of the range of the combustion and the range of the explosion in consideration of the concentration of the reactant and the reaction temperature. The partial pressure of oxygen is from 1 to 6 bar, preferably from 1 to 5 bar based on a gauge basis.

In addition, the gas containing oxygen in the oxidizing gas may contain 10 vol. % or more of oxygen, preferably 60 to 100 vol. %, and more preferably 90 to 100 vol. %. If the oxygen content is less than 60% by volume, there is a problem that the oxidation reaction rate is very slow.

(S2) Oxidation Reaction

Next, the oxidation reaction is carried out to produce acrylic acid.

This oxidation reaction proceeds as shown in Reaction Scheme 1 below and produces acrylic acid as a main product and propionic acid and 3-hydroxypropionic acid as byproducts:

[Reaction Scheme 1]

wherein when using the catalyst of the present invention, 100% of allyl alcohol participates in the oxidation reaction and is converted into acrylic acid in a short time. According to Experimental Example 3 of the present invention, it was measured that the conversion of allyl alcohol was 100% in the reaction time of about 3 hours, and it was confirmed that the yield of acrylic acid was also high.

The reaction temperature is not particularly limited as long as the reaction proceeds in the liquid phase, but it is 10 to 120° C., preferably 20 to 100° C., more preferably 30 to 90° C. If the internal temperature of the reactor is lower than 10° C., the conversion of allyl alcohol is greatly reduced because the rate of oxidation reaction to acrylic acid is very slow. On the contrary, if the temperature is higher than 120° C., there is a problem that the byproducts due to side reactions (i.e., propionic acid, 3-hydroxypropionic acid) are significantly increased in accordance with the increase of the temperature, and the selectivity is greatly reduced.

At this time, the oxidation reaction is performed for 1 to 10 hours, preferably for 2 to 5 hours, and the acrylic acid can be recovered at the conversion of allyl alcohol of 100% and the high yield within the time range. It can be seen that the process time is drastically shortened compared to the reaction time of at least 12 hours, usually 30 hours in the prior art.

(S3) Separation and Recovery of Acrylic Acid

Next, acrylic acid is separated and recovered from the products obtained above.

The acrylic acid prepared in this step is not in the form of an acrylate (i.e., salt of acrylic acid) as in the conventional method, but is obtained in the form of acrylic acid. As a result, there is an advantage that it is possible to exclude the essential processes in the prior art, such as the additional process for converting the acrylate to acrylic acid, i.e., the ion exchange process after the acidification process, thereby reducing the overall process cost.

The separation process of acrylic acid is not particularly limited in the present invention, and a known method in the art can be used.

As an example, the separation process can be carried out by extraction, crystallization or fractional distillation.

The solvent used in the extraction method may include, but is not limited thereto, at least one selected from the group consisting of alcohols, aldehydes, ketones, ethers, esters, aromatic compounds and other organic solvents.

The crystallization is a separating method using the difference in solubility of the mixture, and may include suspension crystallization and layer crystallization method.

The fractional distillation is a separating method using the boiling point difference of the mixture and can be carried out under reduced pressure, normal pressure and high pressure. Solvent may be added to improve separation efficiency. Reactive distillation may be used to simultaneously affect the reaction and separation.

The acrylic acid thus separated can be used as a raw material for organic synthetic materials in various fields.

Additionally, 3-hydroxypropionic acid produced in the above step can be recovered after conversion to acrylic acid through a dehydration reaction using a catalyst by the method described in Korean Laid-Open Patent Application No. 2015-6349.

The acrylic acid produced through the above steps can be applied as a raw material for various chemical products.

Hereinafter, the present invention will be described in more detail with reference to the following examples. However, the following examples should not be construed as limiting the scope of the present invention, and should be construed to facilitate understanding of the present invention.

Preparation Example 1: Preparation of Au/MgO Supported Catalyst 19.7 mg of $HAuCl_4 \cdot 3H_2O$ (99.9%) and 5 ml of an aqueous solution of HCl (0.2 molar concentration) were added to the reactor and mixed uniformly for 10 minutes.

5 g (4 wt. %) of aqueous solution of starch prepared in advance was added to the mixed solution, and the mixture was uniformly mixed for 30 minutes.

After adjusting the pH to 7 by adding 0.5 ml of 1 M NaOH aqueous solution to the mixture obtained, the temperature of the reactor was raised and the reduction reaction was carried out under reflux conditions for 2 hours to prepare an Au catalyst.

After completion of the reaction, 0.5 g of MgO (manufactured by Sigma-Aldrich) was added as a support without lowering the temperature, and the mixture was maintained as it was for 1 hour, and then the reaction was terminated and cooled to room temperature to prepare an Au/MgO catalyst.

The dispersion in which the obtained Au/MgO catalyst is dispersed was centrifuged to recover the catalyst, and dried for 4 days under reduced pressure to prepare the title catalyst.

Preparation Example 2: Preparation of $Au_1Pd_{20.7}$/MgO Supported Catalyst The title catalyst was prepared using the same procedure as Preparation Example 1 above, except that 1 mg of $HAuCl_4 \cdot 3H_2O$ (99.9%) and 8 mg of $PdCl_2$ (99%) were used as precursors.

Preparation Example 3: Preparation of $Au_1Pd_{9.1}$/MgO Supported Catalyst

The title catalyst was prepared using the same procedure as Preparation Example 2 above, except that the mole ratio of the precursors is different.

Preparation Example 4: Preparation of $Au_1Pd_{3.7}$/MgO Supported Catalyst

The title catalyst was prepared using the same procedure as Preparation Example 2 above, except that the mole ratio of the precursors is different.

Preparation Example 5: Preparation of $Au_1Pd_{1.5}$/MgO Supported Catalyst

The title catalyst was prepared using the same procedure as Preparation Example 2 above, except that the mole ratio of the precursors is different.

Preparation Example 6: Preparation of $Au_1Pd_{0.4}$/MgO Supported Catalyst

The title catalyst was prepared using the same procedure as Preparation Example 2 above, except that the mole ratio of the precursors is different.

Preparation Example 7: Preparation of Pd/MgO the Supported Catalyst

The title catalyst was prepared using the same procedure as Preparation Example 1 above, except that 9 mg of $PdCl_2$ (99%) is used as a precursor.

Preparation Example 8: Preparation of $Pd/Mg(OH)_2$ Supported Catalyst

The title catalyst was prepared using the same procedure as Preparation Example 7 above, except that $Mg(OH)_2$ instead of MgO is used as a support.

Preparation Example 9: Preparation of $Pd/Al_2O_3$ Supported Catalyst

The title catalyst was prepared using the same procedure as Preparation Example 7 above, except that $Al_2O_3$ instead of MgO is used as a support.

Preparation Example 10: Preparation of Pd/HT Supported Catalyst

The title catalyst was prepared using the same procedure as Preparation Example 7 above, except that $HT(Mg_4Al_2(CO_3)(OH)_{16} \cdot 4H_2O)$ instead of MgO is used as a support.

Preparation Example 11: Preparation of Pd/HAP Supported Catalyst

The title catalyst was prepared using the same procedure as Preparation Example 7 above, except that $HAP(Ca_5(OH)(PO_4)_3)$ instead of MgO is used as a support.

Preparation Example 12: Preparation of Pd/ZnO Supported Catalyst

The title catalyst was prepared using the same procedure as Preparation Example 7 above, except that ZnO instead of MgO is used as a support.

Preparation Example 13: Preparation of $Pd/Zr(OH)_2$ Supported Catalyst

The title catalyst was prepared using the same procedure as Preparation Example 7 above, except that $Zr(OH)_2$ instead of MgO is used as a support.

Experimental Example 1: Analysis of Mole Ratio and Particle Size

The particle sizes of the supported catalyst particles prepared in the Preparation Examples are shown in Table 1 below.

Figure 2:
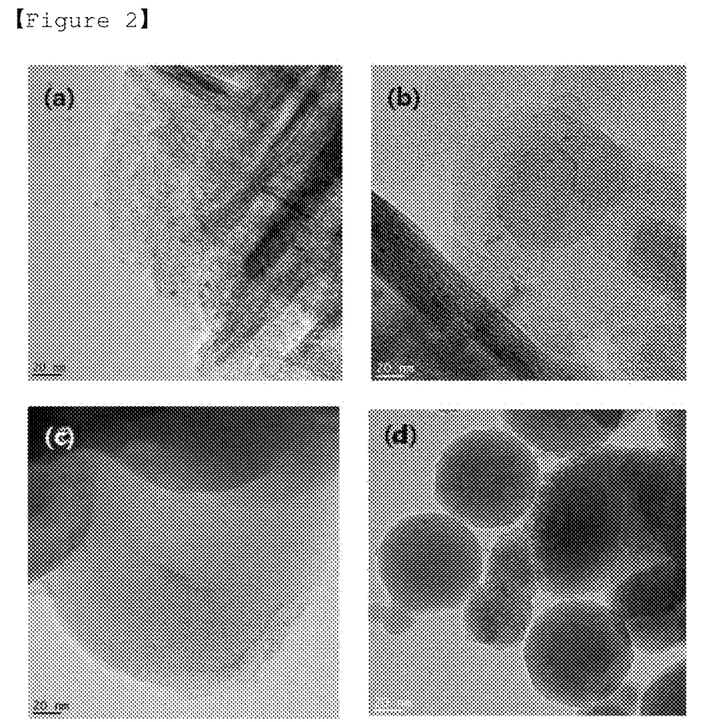
FIG. 2 shows images obtained from the transmission electron microscope for the supported catalysts of (a) preparation example 7 (Pd/MgO), (b) preparation example 8 (Pd/Mg(OH)$_2$), (c) preparation example 10 (Pd/HT) and (d) preparation example 11 (Pd/HAP).

The size of the catalyst was observed using a transmission electron microscope (TEM) (see, FIG. 2).

TABLE 1

| | Supported catalyst | Supported catalyst particle size |
|---|---|---|
| Preparation Example 1 | Au/MgO | 2.2 nm |
| Preparation Example 2 | $Au_1Pd_{20.7}$/MgO | 2.6 nm |
| Preparation Example 3 | $Au_1Pd_{9.1}$/MgO | <2 nm |
| Preparation Example 4 | $Au_1Pd_{3.7}$/MgO | <2 nm |
| Preparation Example 5 | $Au_1Pd_{1.5}$/MgO | <2 nm |
| Preparation Example 6 | $Au_1Pd_{0.4}$/MgO | 2.0 nm |
| Preparation Example 7 | Pd/MgO | 2.2 nm |
| Preparation Example 8 | $Pd/Mg(OH)_2$ | 2.6 nm |
| Preparation Example 9 | $Pd/Al_2O_3$ | 3.0 nm |
| Preparation Example 10 | Pd/HT | <2.0 nm |
| Preparation Example 11 | Pd/HAP | <2 nm |
| Preparation Example 12 | Pd/ZnO | 2.3 nm |
| Preparation Example 13 | $Pd/Zr(OH)_2$ | 2.3 nm |

Referring to Table 1, it can be seen that the supported catalyst prepared in the present invention is a very small particle having a thickness of about 2 nm.

FIG. 2 shows images obtained from the transmission electron microscope for the supported catalysts of (a) preparation example 7 (Pd/MgO), (b) preparation example 8 ($Pd/Mg(OH)_2$), (c) preparation example 10 (Pd/HT) and (d) preparation example 11 (Pd/HAP). Referring to FIG. 2, it can be seen that in the case of the supported catalyst, the particle size was almost uniformly prepared, and thus the catalyst activity of the supported catalyst according to the present invention can be constantly exhibited.

Example 1 to 12: Preparation of Acrylic Acid

Acrylic acid was prepared under the neutral condition using the supported catalysts prepared in Preparation Examples 2 to 13 (see, Table 2).

The supported catalyst, 0.2 ml of allyl alcohol, and 5 ml of distilled water were injected into the reactor. At this time, the molar ratio of allyl alcohol/metal catalyst was set to be 287.

Thereafter, the pressure inside the reactor was reduced, and then oxygen gas was injected to 3 bar, the temperature in the reactor was raised to 50° C., and an oxidation reaction was performed. After completion of the reaction, acrylic acid obtained was purified through fractional distillation.

TABLE 2

| Example | Used supported catalyst |
|---|---|
| Example 1 | $Au_1Pd_{20.7}$/MgO (Preparation Example 2) |
| Example 2 | $Au_1Pd_{9.1}$/MgO (Preparation Example 3) |
| Example 3 | $Au_1Pd_{3.7}$/MgO (Preparation Example 4) |
| Example 4 | $Au_1Pd_{1.5}$/MgO (Preparation Example 5) |
| Example 5 | $Au_1Pd_{0.4}$/MgO (Preparation Example 6) |
| Example 6 | Pd/MgO (Preparation Example 7) |
| Example 7 | $Pd/Mg(OH)_2$ (Preparation Example 8) |
| Example 8 | $Pd/Al_2O_3$ (Preparation Example 9) |
| Example 9 | Pd/HT (Preparation Example 10) |
| Example 10 | Pd/HAP (Preparation Example 11) |
| Example 11 | Pd/ZnO (Preparation Example 12) |
| Example 12 | $Pd/Zr(OH)_2$ (Preparation Example 13) |

Comparative Example 1: Preparation of Acrylic Acid

Acrylic acid was prepared using the same procedure as Example 1 to 12 above, except that the Au/MgO catalyst of Preparation Example 1 is used.

Experimental Example 2: Analysis of Conversion of Allyl Alcohol and Yield of Acrylic Acid According to the Type of Catalyst The conversions of allyl alcohol and yields of acrylic acid prepared in Examples 1 to 6 and Comparative Example 1 were calculated and the results are summarized in Table 3 below.

Figure 3:
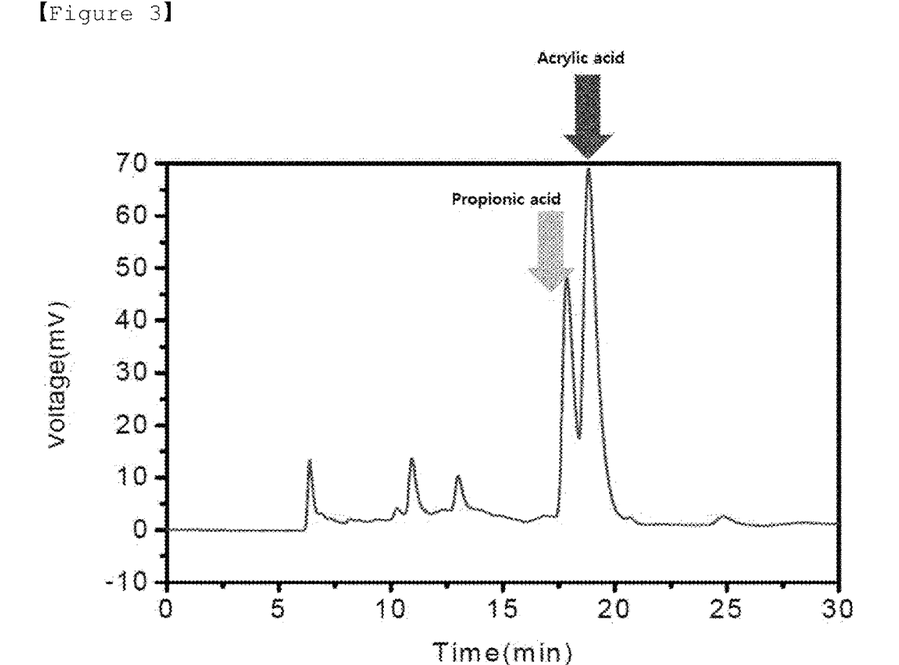
FIG. 3 shows a spectrum obtained from HPLC (High Performance Liquid Chromatography) for the product of the oxidation reaction of allyl alcohol using the catalyst prepared in Example 2.

The conversion of allyl alcohol and the yield of acrylic acid were determined by HPLC (High Performance Liquid Chromatography) analysis. The conversion of allyl alcohol is the molar ratio of allyl alcohol consumed during the reaction to allyl alcohol fed before the reaction, and a conversion of 100% means that all allyl alcohol has participated in the reaction. In addition, propionic acid and 3-HPA are produced as side reaction products of the oxidation reaction (see, HPLC analysis in FIG. 3).

TABLE 3

| | | Conversion | Yield (%) | | |
|---|---|---|---|---|---|
| | Supported catalyst | of allyl alcohol (%) | Acrylic acid | Propionic acid | 3-HPA |
| Comparative Example 1 | Au/MgO | 62.0 | — | — | — |
| Example 1 | $Au_1Pd_{20.7}$/MgO | 100 | 17.7 | 15.8 | 3.1 |
| Example 2 | $Au_1Pd_{9.1}$/MgO | 100 | 18.3 | 17.5 | 3.3 |
| Example 3 | $Au_1Pd_{3.7}$/MgO | 100 | 18.0 | 15.2 | 3.3 |
| Example 4 | $Au_1Pd_{1.5}$/MgO | 100 | 13.3 | 11.6 | 3.5 |
| Example 5 | $Au_1Pd_{0.4}$/MgO | 100 | 5.1 | 9.4 | 1.3 |
| Example 6 | Pd/MgO | 100 | 24.2 | 20.9 | 5.1 |

Referring to Table 3, when the Au/MgO of Comparative Example 1 was used as the supported catalyst, the conversion of allyl alcohol was very low and no conversion to acrylic acid was achieved under the neutral condition.

In comparison with Examples 1 to 6, it can be seen that when Au-transition metal and transition metal catalyst were used, 100% of allyl alcohol was participated in the reaction and the yield of acrylic acid was also high.

In particular, when Pd/MgO of Example 6 was used, the yield of acrylic acid was as high as 24.2%.

Additionally, referring to Examples 1 to 5, the yields were varied depending on the mole ratio of Au—Pd, and there was a trend that the higher the molar ratio of Pd than Au, the higher the yield of acrylic acid was.

Figure 4:
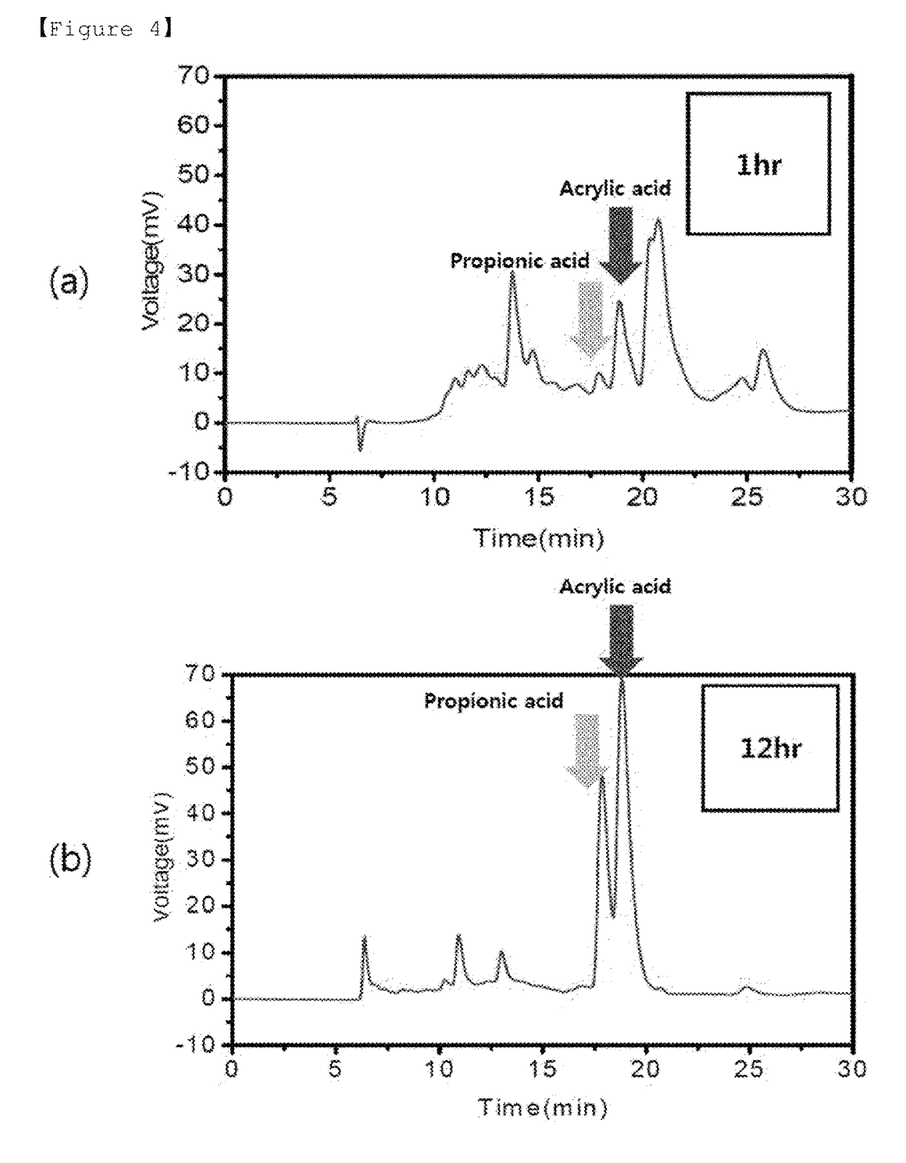

Experimental Example 3: Analysis of Oxidation Reaction of Allyl Alcohol According to Catalyst Reaction Time In order to confirm the reactivity of the supported catalyst according to the present invention, products were collected according to the reaction time to measure the conversion of allyl alcohol and the yield of acrylic acid, and the results are shown in Table 4 and FIG. 4. FIG. 4(a) shows a spectrum obtained from HPLC for the prepared product after the oxidation reaction for 1 hour in Example 3, and FIG. 4(b) is the HPLC spectrum after 12 hours.

TABLE 4

| Supported catalyst | Reaction time (hr) | Conversion of allyl alcohol (%) | Yield (%) Acrylic acid | Yield (%) Propionic acid | Yield (%) 3-Hydroxy propionic acid |
|---|---|---|---|---|---|
| Example 3 ($Au_1Pd_{3.7}$/MgO) | 3 | 100 | 13.9 | 6.9 | 2.2 |
|  | 6 | 100 | 15.9 | 9.9 | 4.1 |
|  | 12 | 100 | 18.1 | 13.2 | 3.8 |
| Example 6 (Pd/MgO) | 1 | 92.4 | 11.6 | 1.3 | 1.7 |
|  | 3 | 94.5 | 18.5 | 11.3 | 2.5 |
|  | 12 | 100 | 24.2 | 20.9 | 5.1 |

Referring to Table 4 and FIG. 4, it can be seen that for the catalyst of Example 3, 100% of allyl alcohol participates in the reaction within 3 hours, and the yield of acrylic acid increases with time.

In comparison, it was exhibited that when the Pd/MgO catalyst of Example 6 was used, the conversion during the 1 hour-reaction was 90% or more.

Particularly, considering the same reaction time, it can be seen that since the yield of acrylic acid after 12 hours was 18.1% for Example 3 and 24.2% for Example 6, when the Pd/MgO supported catalyst was used, the higher yield was obtained.

Experimental Example 4: Test for the Yield of Acrylic Acid and the Durability of the Supported Catalyst According to the Type of Support In order to confirm the durability of the supported catalyst according to the kind of support, the catalyst was prepared by changing the kind of support as follows and used in the production of acrylic acid.

After completion of the production of acrylic acid, the catalyst was recovered and the loss of metal contents of these catalysts was measured using ICP-OES (Inductively Coupled Plasma Atomic Emission Spectroscopy). The results are shown in Table 5 below. At this time, the lower loss of metal content, the better durable the catalyst is.

TABLE 5

| Example | Supported catalyst | Reaction time (h) | Yield of acrylic acid (%) | Element | Loss (%) |
|---|---|---|---|---|---|
| Example 3 | $Au_1Pd_{3.7}$/MgO | 12 | 18.0 | Mg | 22.3 |
| Example 7 | Pd/Mg(OH)$_2$ | 6 | 20.0 | Mg | 31.4 |
| Example 8 | Pd/Al$_2$O$_3$ | 6 | 6.4 | Al | 2.8 |
| Example 9 | Pd/HAP | 6 | 5.6 | Ca | 8.7 |
| Example 10 | Pd/ZnO | 12 | 17.8 | Zn | 39 |
| Example 11 | Pd/Zr(OH)$_2$ | 12 | 2.4 | Zr | — |

As shown in Table 5, it was found that the yields of acrylic acid differ depending on the type of support.

Specifically, when the Pd catalysts were supported on Mg(OH)$_2$ and ZnO, the yield of acrylic acid in the same time was high, but the loss of Mg and Zn occurred at a high level. Also, when comparing Examples 3 and 7, there was a trend that the Mg loss rate was slightly lower when Mg was used as the oxide form of MgO.

Also, as can be seen from Examples 8 and 11, there was a trend that when Al$_2$O$_3$ and Zr(OH)$_2$ were used as support, there was little or no loss after 12 hours reaction, but the production yield of acrylic acid was lower than other supports.

The catalyst according to the present invention is applicable to the preparation industry of acrylic acid which is a raw material of an organic synthetic material.

The invention claimed is:

1. A method for preparing acrylic acid, the method comprising oxidizing allyl alcohol in the presence of a catalyst at a pH of 6-8, wherein:
the catalyst is a supported catalyst in which a metal catalyst is supported on a support;
the metal catalyst is selected from the group consisting of an Au-transition metal alloy catalyst, a transition metal catalyst, and a combination thereof; and
the support is selected from the group consisting of MgO, Mg(OH)$_2$, Al$_2$O$_3$, cHT (calcined hydrotalcite), hydroxyapatite(Ca$_5$(OH)(PO$_4$)$_3$), ZnO, Zr(OH)$_2$ and a combination thereof.

2. The method for preparing acrylic acid according to claim 1, characterized in that the supported catalyst is used so that the molar ratio of the allyl alcohol to metal catalyst is 10:1 to 2000:1.

3. The method for preparing acrylic acid according to claim 1, characterized in that the transition metal is selected from the group consisting of Ru, Rh, Pd, Os, Ir, Pt, Zn, Co, Ni, Cr, Fe, Mo, Nb, Mn and a combination thereof.

4. The method for preparing acrylic acid according to claim 1, characterized in that the metal catalyst has a particle size of 1 to 50 nm.

5. The method for preparing acrylic acid according to claim 1, characterized in that the supported catalyst has the metal catalyst supported in an amount of 0.0001 to 5 wt % based on the total dry weight of the support.

6. The method for preparing acrylic acid according to claim 1, characterized in that the supported catalyst is prepared by impregnating the support with a metal catalyst prepared by a colloid nano particle deposition (colloid deposition) method.

7. The method for preparing acrylic acid according to claim 1, characterized in that the oxidation reaction is performed by injecting an oxidizing gas.

8. The method for preparing acrylic acid according to claim 7, characterized in that the oxidizing gas is oxygen or an oxygen-containing gas.

9. The method for preparing acrylic acid according to claim 7, characterized in that the oxidizing gas is injected to a gauge pressure of 1 to 6 bar.

10. The method for preparing acrylic acid according to claim 1, characterized in that the oxidation reaction is carried out at 10 to 120° C.

* * * * *

UNITED STATES PATENT AND TRADEMARK OFFICE
CERTIFICATE OF CORRECTION

PATENT NO. : 10,266,475 B2
APPLICATION NO. : 15/752181
DATED : April 23, 2019
INVENTOR(S) : Won Jae Lee et al.

Page 1 of 1

It is certified that error appears in the above-identified patent and that said Letters Patent is hereby corrected as shown below:

On the Title Page

Item (73) Assignee should read:
LG CHEM, LTD., Seoul (KR)
KOREA ADVANCED INSTITUTE OF SCIENCE AND TECHNOLOGY, DAEJEON (KR)

Signed and Sealed this
Fourteenth Day of April, 2020

Andrei Iancu
*Director of the United States Patent and Trademark Office*